(12) United States Patent
Lehmikangas et al.

(10) Patent No.: US 6,311,550 B1
(45) Date of Patent: Nov. 6, 2001

(54) METHOD FOR MEASURING PARTICLES IN SUSPENSION AND MEASURING INSTRUMENT

(75) Inventors: Keijo Lehmikangas, Puolanka; Lauri Löytynoja, Kajaani, both of (FI)

(73) Assignee: Metso Field Systems Oy, Helsinki (FI)

( * ) Notice: Subject to any disclaimer, the term of this patent is extended or adjusted under 35 U.S.C. 154(b) by 0 days.

(21) Appl. No.: 09/154,914

(22) Filed: Sep. 17, 1998

(30) Foreign Application Priority Data

Sep. 22, 1997 (FI) .......................................... 973753

(51) Int. Cl.$^7$ .......................... G01N 15/06; G01N 21/00; G01B 11/00
(52) U.S. Cl. ........................... 73/61.71; 356/338; 356/394
(58) Field of Search ................................ 79/61.71, 61.72; 356/338, 343, 335, 334, 394

(56) References Cited

U.S. PATENT DOCUMENTS

| | | | |
|---|---|---|---|
| 4,066,492 | 1/1978 | Hill | 162/49 |
| 4,266,874 | 5/1981 | Janin et al. | 356/335 |
| 4,837,446 | 6/1989 | Renard et al. | 250/461.1 |
| 5,293,219 | 3/1994 | Ayer | 356/383 |
| 5,311,290 | 5/1994 | Olson et al. | 356/383 |
| 5,530,551 | 6/1996 | Cantrall et al. | 356/394 |
| 5,570,181 | 10/1996 | Yasuo et al. | 356/336 |
| 5,786,894 | 7/1998 | Shields et al. | 356/338 |

FOREIGN PATENT DOCUMENTS

| | | |
|---|---|---|
| 0564157 | 10/1993 | (EP) . |
| 0711991 | 5/1996 | (EP) . |
| 57845 | 6/1980 | (FI) . |
| 73081 | 4/1987 | (FI) . |
| 83996 | 6/1991 | (FI) . |
| 9408223 | 4/1994 | (WO) . |

Primary Examiner—Helen Kwok
Assistant Examiner—Jay L. Politzer
(74) Attorney, Agent, or Firm—Ladas & Parry

(57) ABSTRACT

The invention relates to a method for measuring particles in suspension and a measuring instrument. In the solution the length of each fiber-like particle in suspension is one by one optically measured by a line camera in a thin equilateral capillary tube. The fiber-like particles in particular are imaged by two or more cameras in the capillary tube one or more times for measuring such properties as fiber thickness, wall-thickness and fibrillation.

57 Claims, 3 Drawing Sheets

METHOD FOR MEASURING PARTICLES IN SUSPENSION AND MEASURING INSTRUMENT

FIELD OF THE INVENTION

The invention relates to a method for measuring particles in suspension, the suspension comprising at least wood fibers and/or equivalent fibers, in which method each fiber-like particle in a flowing suspension is one by one optically imaged and measured in a substantially equilateral capillary tube.

The invention also relates to a measuring instrument for measuring particles in suspension, the suspension comprising at least wood fibers and/or equivalent fibers, and the measuring instrument comprising a substantially equilateral capillary tube and being arranged to optically measure one by one each fiber-like particle in a flowing suspension in the capillary tube.

BACKGROUND OF THE INVENTION

To ensure paper quality it is important to know the properties of the wood fibers used in paper making. Important properties include fibre length, fibre thickness and fiber wall thickness. Fiber fibrillation is another important feature. According to prior art these properties can usually be measured by a microscope. In addition, the fiber length can also be measured in an automated manner, in which case this method is suitable for rapidly changing industrial circumstances. The length of a fiber or a fiber-like particle is measured by using a line camera and a thin circular capillary tube. The fibers move one by one in a thin tube from which the line camera forms an image on its detector surface. The fiber length can be formed using the number of pixels covering the fiber image. This method is an efficient way of measuring fiber length, but other fiber properties thus remain unmeasured.

BRIEF DESCRIPTION OF THE INVENTION

An object of the invention is thus to provide a method and a measuring instrument implementing the method so as to solve said problems and to measure all important properties of fiber-like particles at the same time if needed.

This is achieved with a method of the type described in the preamble, characterized in that for measuring the length of the fiber-like particle a position of the fiber-like particle is determined and a real image is formed of the fiber-like particles from at least one direction in the equilateral capillary tube one or more times at least for measuring the length and the transverse measure of the fiber-like particles, and the imaging of the transverse measure of the fiber-like particle is controlled by means of the length measurement of the fiber-like particle in order to determine an imaging point.

The measuring instrument of the invention is, in turn, characterized In that the measuring instrument comprises at least two cameras, one of which being arranged to form a real image of the fiber-like particle, to determine the position; and length of the fiber-like particle, and a second camera being arranged to form a real image of the fiber-like particles in the capillary tube one or more times at least for measuring the transverse measure of the fiber-like particles, and the measuring instrument is arranged to control the imaging of the transverse measure of the fiber-like particle by means of the position of the fiber-like particle in order to determine an imaging point.

Several advantages are achieved with the method and instrument of the invention. The solution of the invention can be used to measure length, thickness, wall thickness and fibrillation at the same time. Furthermore, the measures and properties of the fiber can be measured from two different directions. This information allows to accurately define the quality of different wood pulps, for example separately for each wood quality. The lignin content in fibers can also be measured.

BRIEF DESCRIPTION OF THE DRAWINGS

In the following the invention will be described in connection with the preferred embodiments with reference to the accompanying drawings, in which.

DETAILED DESCRIPTION OF THE INVENTION

The measuring method and measuring instrument of the invention are particularly applicable for measuring wood fibers in pulp and paper industry without being restricted thereto.

Figure 1:
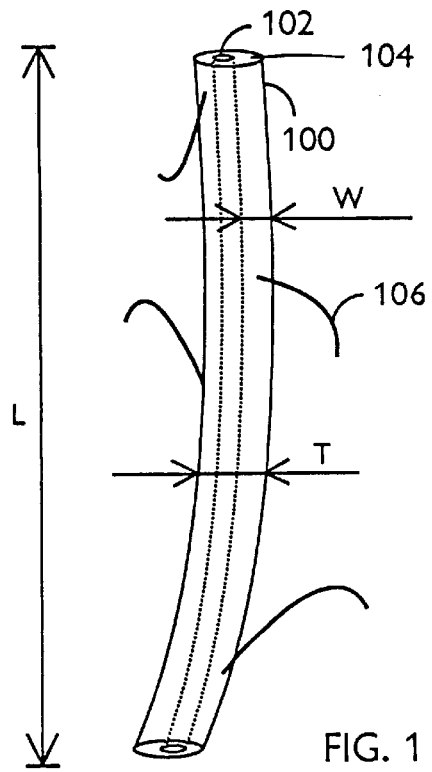
FIG. 1 shows a fiber.

Let us first look closer at an ordinary wood fiber 100 in FIG. 1. The wood fiber 100 comprises a hollow inner part 102, which may also be collapsed. Since the inner part of the fiber 100 is hollow, the fiber 100 comprises a measurable wall 104. In addition the fiber 100 comprises fibrils 106, which form the surface of the fiber and which are able to come off the fiber 100 when the fibers 100 are being processed. In FIG. 1 letter L indicates fiber length, letter T indicates fiber thickness and letter W wall 104 thickness. The average length L of an ordinary northern softwood is approximately 1 mm and the wall 104 thickness W is 5 $\mu$m.

Figure 2:
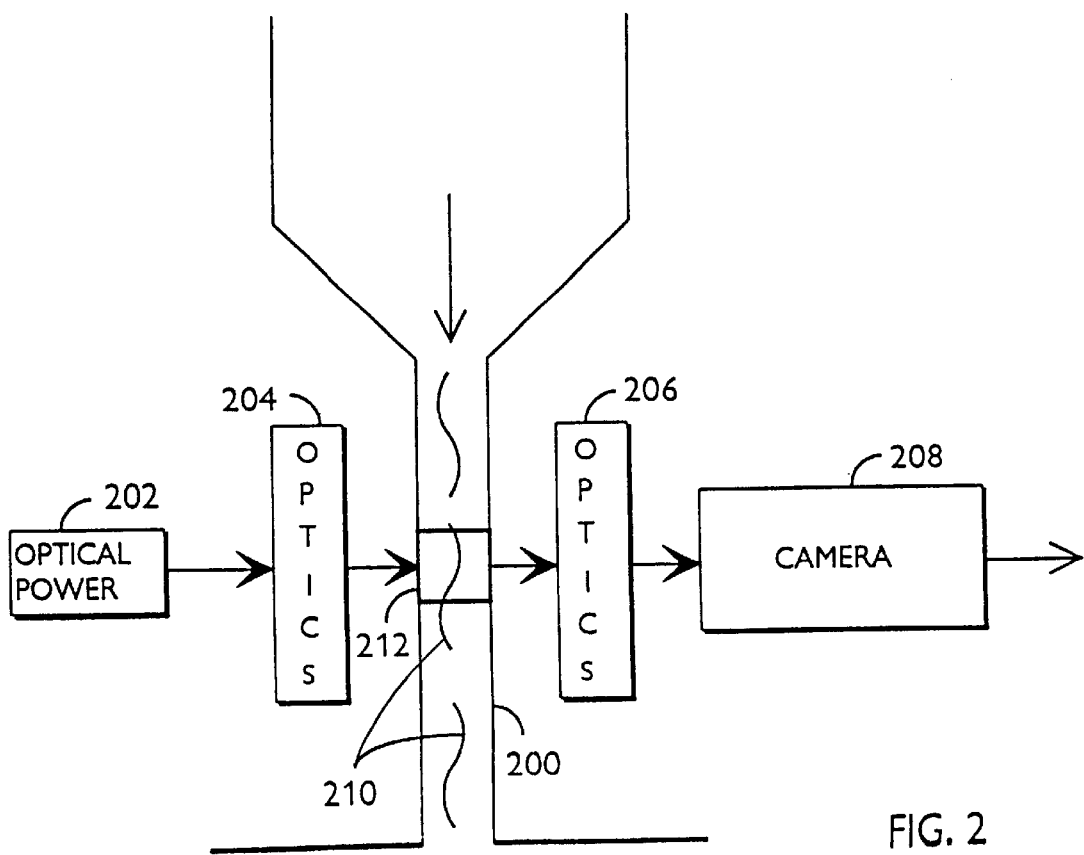
FIG. 2 shows an imaging arrangement.

Let us now examine the imaging arrangement of the invention by means of FIG. 2. The imaging arrangement comprises a capillary tube 200, an optical power source 202, optics 204 and 206 and a camera 208. The optical power source 202 is preferably a source emitting optical power in flashes, like a xenon lamp. The camera 208, in turn, is preferably a CCD camera imaging an imaging point 212 when the lamp 202 flashes. The optics 204 comprising at least a lens or lenses and possibly an aperture for spatially processing the optical power focuses the optical power arriving from the optical power source 202 on the imaging point 212. The optics 206 also comprising at least a lens or lenses and possibly an aperture for spatially processing optical power images the imaging point 212 on the detector surface of the camera 208. One pixel then preferably corresponds to, for example, 1 $\mu$m. The optics 204 and 206 can further comprise different optical filters for adjusting an optical bandwidth and a polarisation, but they are not necessary. In the inventive solution the lamp 202 preferably flashes when a fiber 210 is at the imaging point 212, in which case a partial or total image of the fiber 210 is obtained in the longitudinal direction of the fiber 210. The duration of the flash must be sufficiently short, for example 1 $\mu$s, in order to obtain an accurate image of the moving fiber 210. Instead of a flashing lamp continuous illumination can also be used, in which case the camera 208 uses a short exposure time for taking an image. The exposure has to decrease as the flow in the capillary tube 200 increases. The capillary tube 200 of the invention penetrates optical radiation and is equilateral, preferably quadratic (i.e., a quadrangle and, more preferably, a square) in cross section. The largest inside measure in the direction of the normal of the inner surface is preferably about 0.5 mm. A low consistency suspension, whose consistency ranges, for example, from 0.005 to 0.001% flows downwards in FIG. 2. The flow speed has no significance for the invention, but a typical suitable speed is 5 m/s, whereby up to 100 fibers can be measured per second. The flow can be facilitated by absorbing suspension from the bottom of the tube at low pressure. Then the fibers 210 in suspension flow substantially one by one through the capillary tube 200.

Figure 3:
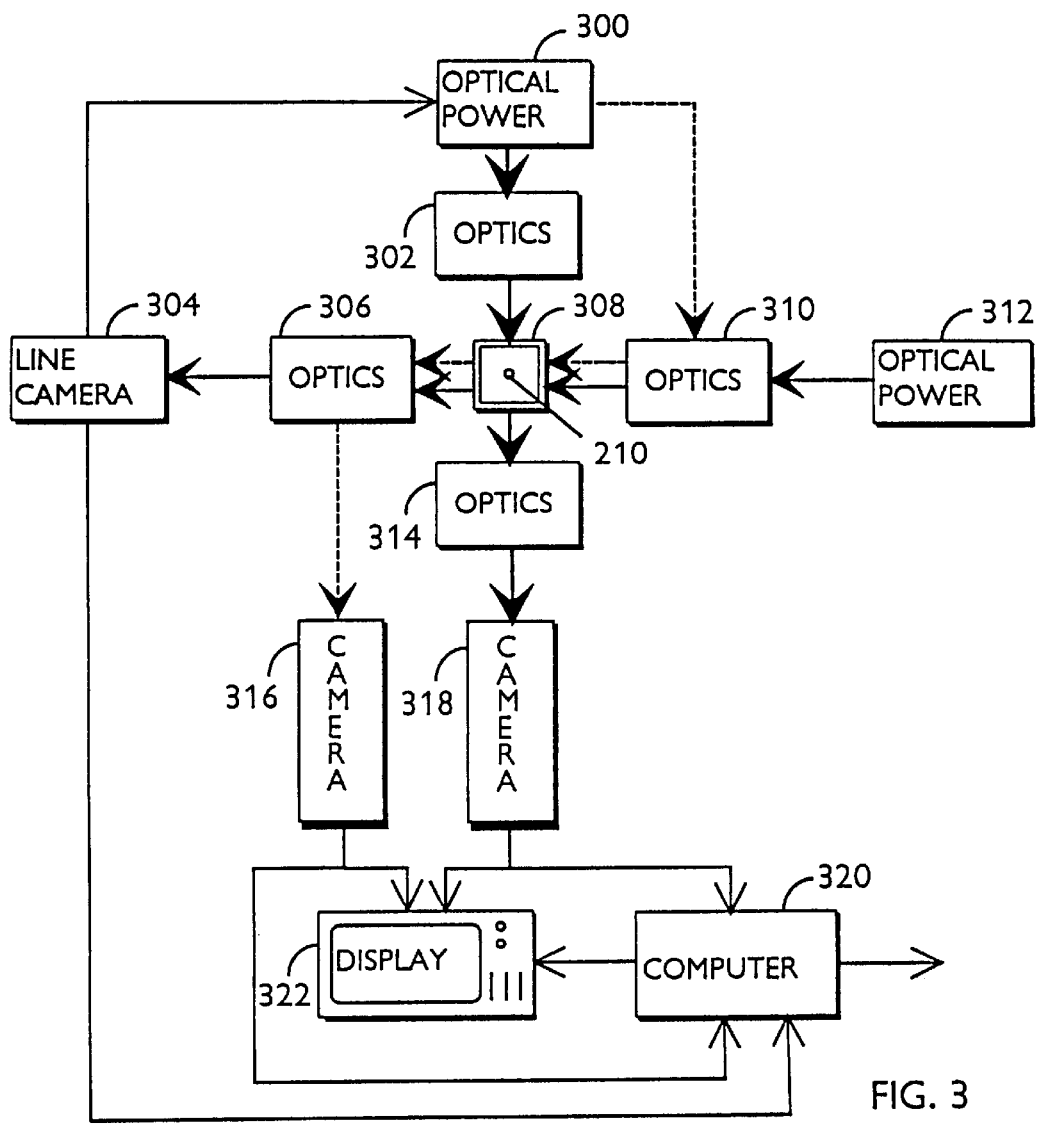
FIG. 3 shows a measuring instrument.

Let us now look closer at the measuring instrument of the invention and explain at the same time the method of the invention by means of FIG. 3, where the optical signals are marked by a thicker arrow than the electrical signal. The measuring instrument comprises at least a first optical power source 300, optics 302, 306, 310 and 314, a first camera 304, a second optical power source 312 and a second camera 318. Let us first look at this part of the arrangement only. The imaging arrangement according to FIG. 2 including the blocks 202, 204, 200, 206 and 208 comprises in FIG. 3 the blocks 300, 302, 308, 314 and 318. According to prior art the length of the fiber is measured as follows. The optical power source 312, for example a HeNe laser, emits radiation to the optics 310 typically comprising an expander collimating a beam, an aperture for spatially processing radiation, a focusing lens and a polarizer. The optics 310 focuses the radiation into an imaging point in the capillary tube 308, from where the radiation proceeds to the optics 306 comprising the polarizer and lenses for imaging the imaging point on the detector surface of the line camera 304. A detector line of the line camera 304 is parallel to the capillary tube, in which case the detector line is able to measure the length, position and movement of the fiber. An acceptable accuracy is achieved when at least the first part of the detector line detects the fiber with an accuracy of 50 µm. The fiber 210 imaging according to FIG. 2 can then be controlled, or scheduled, using the line camera 304 in such a manner that when the line camera 304 has noted that the fiber is at the imaging point, which is preferably the same as the measurement point of the fiber length, the line camera 304 controls the optical power source 300 to flash, and second the camera 318 takes an image of the fiber. Instead of controlling the optical power source 300 the second camera 318 can be controlled to take an image at a short exposure time, in which case the optical power source 300 can be continuous. As the fiber position is known at different times, the fiber can be adaptively imaged one or more times from one or more points. The enlargement of the optics can also be changed manually or automatically, whereby the fiber can be imaged by different enlargements.

Using this solution only the user should process the measurement results manually or separately utilize an automated device such as a calculator or a computer. In addition this solution takes an image of the fiber from one direction only. In order to automate data processing and to take images from two crossing directions the inventive measuring instrument preferably comprises a third camera 316, a computer 320 and a display terminal 322. Then the camera 316 takes an image of the fiber substantially at the same time as the camera 318, but this image is 900° from a different angle. To take an image in this way is possible, as the radiation of the optical power source 300 is divided to arrive at the optics 310 comprising a mirror at a desired angle. This mirror is preferably such that it substantially reflects the radiation arriving from the optical power source 300 before or after the polarizer in the same direction as the radiation arriving from the optical power source 312, but that the mirror penetrates the radiation arriving from the optical power source 312 substantially fully. Thus, the radiation of both optical power sources 300 and 312 proceeds in the same way in the same direction through the capillary tube. The optics 306 comprises a similar mirror which preferably controls before the polarizer the radiation of the optical power source 300 to the camera 316. The images of the cameras 316 and 318 can preferably be seen by the user on the display 322. Furthermore the computer 320 processes the images with an image processing program in order to facilitate the measurement of the properties of the particles at the point where the images are taken, in which case, for example, the outlines are sharpened.

When wood fiber pulp is measured the computer 320 preferably measures from the fibers their longitudinal measure and transverse measures. Then the length, thickness and wall thickness of the fiber are measured. In addition fiber detachment or adhesion to one another can be measured and observed. The computer 320 can also measure the number of fiber fibrils and surface properties and properties of other fibers in suspension, such as amount and size. The other fibers are fillers used in paper making, such as kaolin and fines generated when the fibers are degraded during the manufacturing process of the pulp. Also the number and quality of shives in wood fiber pulp can be measured and observed. The computer 320 processes the measurements it has performed preferably statistically, thus enabling studies on, for example, length and thickness distributions of the fibers. Then, for example, tens of thousands of fibers are measured. In order to improve image processing a reference image is taken for the computer 320 of the capillary containing only water. Then the solid impurities in the capillary can be left unnoticed during the measurements and they can computationally be removed from the image taken of the actual suspension.

With the inventive solution it is possible in addition to the longitudinal and transverse measures of the fiber also to measure the lignin content of the fibers and thus observe, for example, how efficient the bleaching process is at fiber level. The lignin content, the measurement of which is known per se, can be measured, for example, by employing at least two wave lengths in the measurement in such a manner that one wave length is absorbed in the lignin and the other one is not absorbed. A typical absorbing optical bandwidth is preferably in the UV area.

Figure 4:
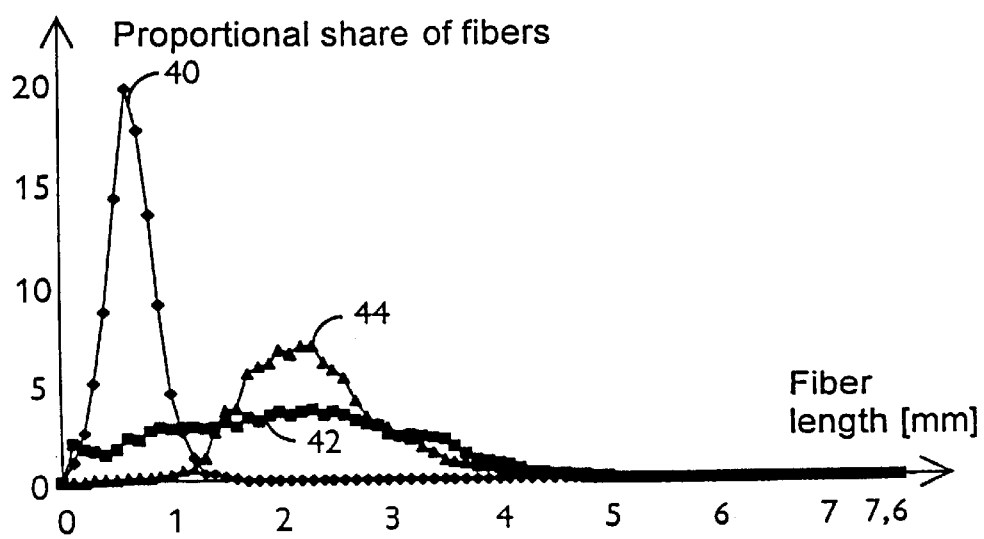
FIG. 4 shows a measurement result of fiber length.
Figure 5:
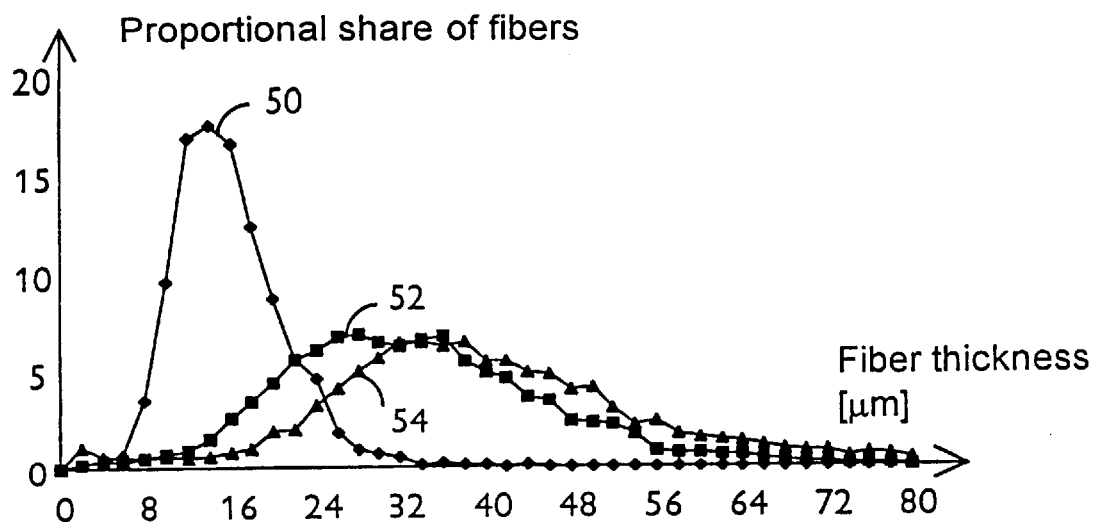
FIG. 5 shows a measurement result of fiber thickness.
Figure 6:
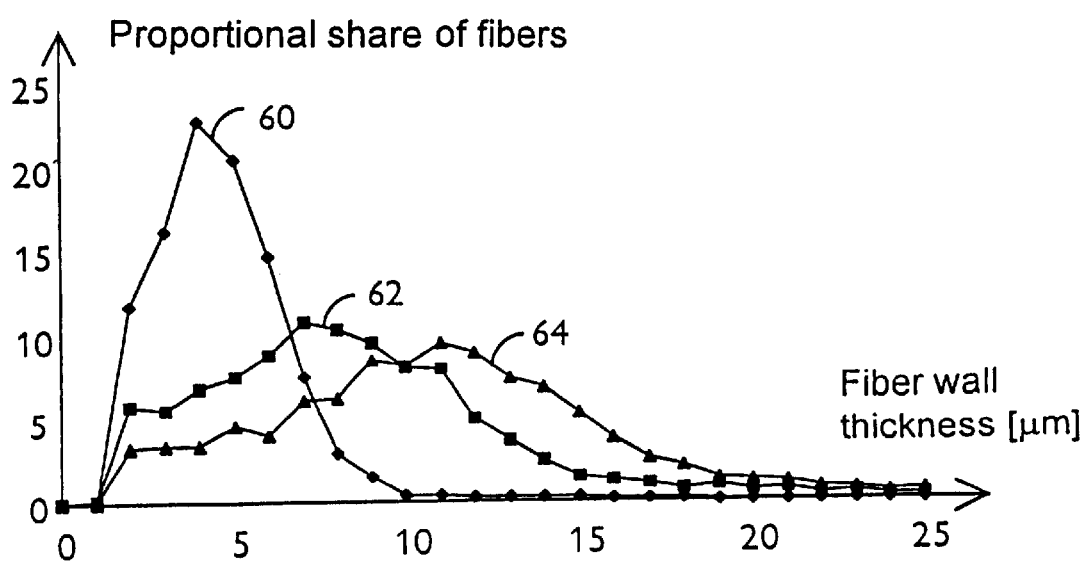
FIG. 6 shows a measurement result of fiber wall thickness.

Let us now take a closer look at the measurement results in FIGS. 4–6 obtained by the inventive solution. FIG. 4 shows a length measurement result of wood fibers according to prior art. A proportional share is on the Y axis and the fiber length between 0 mm–7.6 mm is on the X axis. Curve 40 shows a length distribution of a tropical hardwood. Curve 42 shows a length distribution of a typical northern softwood. Curve 44 shows a length distribution of mechanically processed wood pulp.

FIG. 5 shows thickness distributions measured by the inventive solution. Curve 50 shows a thickness distributions of a tropical hardwood between 0–80 µm, curve 52 shows a thickness distributions of a northern softwood and curve 54 shows a thickness distribution of the mechanical pulp fibers.

FIG. 6 shows fiber wall thickness distributions measured by the inventive solution. Curve 60 shows thickness distributions of the fiber walls of a tropical hardwood between 0–25 on the index scale corresponding fairly accurately to the range 0–17 µm, curve 62 shows a thickness distribution of the fiber walls of a northern softwood and curve 64 shows a thickness distribution of the fiber walls of mechanical pulp. The measurements are performed by measuring dozens of fibers per second and by averaging approximately 30 000 measurements.

The advantage with the invention is that since the fibers are imaged from different directions, the twisting of the fibers can be detected. Twisting affects the wood fiber thickness in particular, since the fibers can be flat. The computer can then easily correct the thickness measurement. Telecentric optics, whose aperture is placed in front of the optics at the focal point, is used as the optics 204, 206, 302, 306, 310 and 314. Then the exit pupil is initially at infinity. The bandwidth of the optical power sources can be wide (hundreds of nanometers) or narrow (10 nm or below). The optical operation area too can range from ultraviolet to infrared. The computer 320 can also control the manufacturing process of paper or pulp by means of measurement data.

In addition to wood fibers the inventive solution is applicable for measuring synthetic fiber properties. In measuring equipment calibration, for example rayon fibers are used, but the inventive solution is also applicable for measuring plastic or metal fiber-like particles.

Even though the invention has been described above with reference to the examples of the accompanying drawings, it is obvious that the invention is not restricted thereto but can be modified in various ways within the scope of the inventive idea disclosed in the attached claims.

What is claimed is:

1. In a method for measuring a fiber-like particle (100, 210) in a suspension flowing in a substantially equilateral cross-section capillary tube (200), the improvements in that:
   for measuring a length and transverse measure of the fiber-like particle (100, 210), a position of the fiber-like particle (100, 210) is determined and a real image is formed of the fiber-like particle (100, 210) in the equilateral cross-section capillary tube (200) one or more times from at least one direction; and
   a measurement point along the fiber-like particle (100, 210) of the transverse measure of the fiber-like particle (100, 210) is adaptively controlled from the length measurement of the fiber-like particle (100, 210).

2. A method as claimed in claim 1, characterized in that the fiber-like particles (100,210) are imaged with a CCD camera (208, 316, 318) in the capillary tube (200) one or more times from at least two different directions substantially at 90° angles from both sides.

3. A method as claimed in claim 2, characterized in that the twisting of the imaged fiber-like particles (100,210) is determined and when the thickness of the fiber-like particle (100,210) is measured the effect of the twisting on average thickness is taken into account.

4. A method as claimed in claim 2, characterized in that wood fiber pulp is measured and the fiber-like particles (100,210) to be imaged are wood fibers.

5. A method as claimed in claim 4, characterized in that the number of shives is measured from the images formed.

6. A method as claimed in claim 4, characterized in that in addition to the measures the fibrillation of the fiber (100,210) and/or other surface properties of the fiber (100, 210) are measured from the images formed.

7. A method as claimed as claimed in claim 4, characterized in that properties of fines and fillers of pulp are measured from the images formed.

8. A method as claimed in claim 4, characterized in that pulp quality is determined on the basis of the measurements.

9. A method as claimed in claim 4, characterized in that pulp is illuminated by at least two different wave lengths and the lignin content of the fiber (100,210) is measured on the basis of the absorption of the wave lengths.

10. A method as claimed in claim 1, characterized in that the thickness as a transverse measure of the imaged fiber-like particles (100,210) is measured from one or more positions.

11. A method as claimed in claim 1, characterized in that the wall thickness as a transverse measure of the image fiber-like particles (100,210) is measured from one or more positions.

12. A method as claimed in claim 1, characterized in that in addition to the measures the detachment of the imaged fiber-like particles (100,210) is measured.

13. A method as claimed in claim 1, characterized in that wood fiber pulp is measured and the fiber-like particles (100,210) to be imaged are wood fibers.

14. A method as claimed in claim 13, characterized in that the number of shives is measured from the images formed.

15. A method as claimed in claim 13, characterized in that in addition to the measures the fibrillation of the fiber (100,210) and/or other surface properties of the fiber (100, 210) are measured from the images formed.

16. A method as claimed as claimed in claim 13, characterized in that properties of fines and fillers of pulp are measured from the images formed.

17. A method as claimed in claim 13, characterized in that pulp quality is determined on the basis of the measurements.

18. A method as claimed in claim 13, characterized in that pulp is illuminated by at least two different wave lengths and the lignin content of the fiber (100,210) is measured on the basis of the absorption of the wave lengths.

19. A method as claimed in claim 1, characterized in that the fiber-like particles (21) which are synthetic fibers are imaged and measured.

20. A method as claimed in claim 1, characterized in that the properties of the imaged particles (100,210) are measured by an image processing program and the properties are statistically processed.

21. A method as claimed in claim 1, characterized in that images taken of the fiber-like particles (100,210) are shown to the user.

22. A method as claimed in claim 1, characterized in that the cross section of the capillary tube (200) is a quadrangle and preferably a square.

23. A method as claimed in claim 1, characterized in that the fiber-like particles (100,210) are imaged with a line camera (304) determining the length of the fiber-like particle (100,210).

24. A method as claimed in claim 23, characterized in that the imaging of the length and transverse measure of the fiber-like particle (100,210) is adaptively controlled by means of the position information based on the length measurement in such a manner that the imaging is performed only when the fiber-like particle (100,210) is at a desired at least one imaging point.

25. In a measuring instrument for measuring a fiber-like particle (100, 210) in a flowing suspension in a substantially equilateral cross-section capillary tube (200), the improvements comprising:
   at least one camera (304) to determine the position and length of the fiber-like particle (100, 210), and a second camera to form a real image of the fiber-like particle (100, 210) in the capillary tube (200) one or more times at least for measuring the transverse measure of the fiber-like particle (100, 210), wherein the length measurement of the fiber-like particle (100, 210) adaptively controls the measurement point of the transverse measure on the fiber-like particle (100, 210).

26. A measuring instrument as claimed in claim 25, characterized in that the measuring instrument comprises at least two cameras (208,316,318) for imaging the fiber-like particles (110,210) in the capillary tube (200) one or more times substantially at 90° angles from both sides.

27. A measuring instrument as claimed in claim 26, characterized in that the measuring instrument comprises a computer (32) arranged to measure the thickness of the fiber-like particle (100,210) as a transverse measure from at least one position.

28. A measuring instrument as claimed in claim 27, characterized in that the computer (320) is arranged to measure from the images the wall thickness of the fiber-like particle (100,210) as a transverse measure from one or more positions.

29. A measuring instrument as claimed in claim 27, characterized in that the computer (320) is arranged to determine from the images the twisting of the fiber-like particle (100,210) and the computer (320) is arranged to observe the effect of the twisting on average thickness.

30. A measuring instrument as claimed in claim 27, characterized in that the computer (320) is arranged to measure in addition to the measures the detachment of the fiber-like particles (100,210) from the images.

31. A measuring instrument as claimed in claim 27, characterized in that the measuring instrument is arranged to measure suspension that is wood fiber pulp and the fiber-like particles (100,210) to be imaged are wood fibers.

32. A measuring instrument as claimed in claim 31, characterized in that the computer (320) is arranged to measure the number of shives from the images.

33. A measuring instrument as claimed in claim 31, characterized in that the computer (320) is arranged to measure from the images in addition to the measures the fibrillation of the fiber and/or other surface properties of the fiber.

34. A measuring instrument as claim in claim 31, characterized in that the computer is arranged to measure from the images the properties of fines and fillers.

35. A measuring instrument as claimed in claim 31, characterized in that the computer (320) is arranged to determine pulp quality on the basis of the measured data.

36. A measuring instrument as claimed in claim 31, characterized in that when pulp is illuminated by at least two different wave lengths the computer (320) is arranged to measure the lignin content of the fiber (100,210) from the images.

37. A measuring instrument as claimed in claim 27, characterized in that the computer (320) is arranged to measure the properties of the imaged particles (100,210) by an image processing program and to statistically process the properties.

38. A measuring instrument as claimed in claim 25, characterized in that the measuring instrument comprises a computer (32) arranged to measure the thickness of the fiber-like particle (100,210) as a transverse measure from at least one position.

39. A measuring instrument as claimed in claim 38, characterized in that the computer (320) is arranged to measure from the images the wall thickness of the fiber-like particle (100,210) as a transverse measure from one or more positions.

40. A measuring instrument as claimed in claim 38, characterized in that the computer (320) is arranged to determine from the images the twisting of the fiber-like particle (100,210) and the computer (320) is arranged to observe the effect of the twisting on average thickness.

41. A measuring instrument as claimed in claim 38, characterized in that the computer (320) is arranged to measure in addition to the measures the detachment of the fiber-like particles (100,210) from the images.

42. A measuring instrument as claimed in claim 38, characterized in that the measuring instrument is arranged to measure suspension that is wood fiber pulp and the fiber-like particles (100,210) to be imaged are wood fibers.

43. A measuring instrument as claimed in claim 42, characterized in that the computer (320) is arranged to measure the number of shives from the images.

44. A measuring instrument as claimed in claim 42, characterized in that the computer (320) is arranged to measure from the images in addition to the measures the fibrillation of the fiber and/or other surface properties of the fiber.

45. A measuring instrument as claim in claim 42, characterized in that the computer is arranged to measure from the images the properties of fines and fillers.

46. A measuring instrument as claimed in claim 42, characterized in that the computer (320) is arranged to determine pulp quality on the basis of the measured data.

47. A measuring instrument as claimed in claim 42, characterized in that when pulp is illuminated by at least two different wave lengths the computer (320) is arranged to measure the lignin content of the fiber (100,210) from the images.

48. A measuring instrument as claimed in claim 38, characterized in that the computer (320) is arranged to measure the properties of the imaged particles (100,210) by an image processing program and to statistically process the properties.

49. A measuring instrument as claimed in claim 25, characterized in that the measuring instrument is arranged to image and measure suspension in which the fiber-like particles (210) are synthetic fibers.

50. A measuring instrument as claimed in claim 25, characterized in that the measuring instrument comprises a display (322) and the measuring instrument is arranged to show on the display (312) images of the fiber-like particles (100,210) taken by at least one camera (208, 316, 318) to the user.

51. A measuring instrument as claimed in claim 25, characterized in that the cross section of the capillary tube (200) is a quadrangle and preferably a square.

52. A measuring instrument as claimed in claim 25, characterized in that the measuring instrument comprises a line camera (304) or the like for measuring the length of the fiber-like particle (100,210).

53. A measuring instrument as claimed in claim 52, characterized in that for measuring the length of the fiber-like particle (100,210) the line camera (304) is arranged to determine the position of the fiber-like particle (100,210) and the line camera (304) is arranged to adaptively control the imaging of the length and transverse measure of the fiber-like particle (100,210) by means of the position information obtained on the basis of the length measurement of the fiber-like particle (100,210) in such a manner that one camera (316,318) is arranged to image only when the fiber-like particle (100,210) is at a desired at least one imaging point.

54. In a method for measuring fiber-like particles in a flowing suspension, the improvements comprising:

optically imaging the particles one by one in the flowing suspension in a substantially equilateral capillary tube; and determining a position of the each of the particles when optically imaged and forming A real image thereof from at least one direction one or more times for measuring a length and transverse measure thereof, p1 wherein the imaging for the transverse measure is controlled by the length measurement in order to determine a measurement point along each of the particles at which the transverse measure of each of the particles is measured, and wherein the imaging for the length and transverse measure of the particle is adaptively controlled by the determined position based on the length such that the imaging occurs only when each of the particles is at an imaging point.

55. A measuring instrument for measuring a particle in a suspension, the measuring instrument comprising:

a substantially equilateral capillary tube for receiving a flow of the suspension;

at least first and second cameras, the first camera being arranged to form a real image of the particle for determining a position and length of the particle, and the second camera being arranged to form a real image of the particle in the tube one or more times at least for measuring a transverse measure of the particle;

means for controlling the image formed by the second camera from the determined position and determining a measurement point along the particles for the transverse measure; and means for adaptively controlling the image and determining the length and transverse measure from the position on the basis of the length measurement of the particle in such a manner that the second camera is arranged to image the particle only when the particle is at a desired at least one imaging point.

56. A method for measuring particles in suspension, the method comprising a length measurement and a transverse measurement of a particle using the steps of:

flowing suspended particles one by one in a substantially equilateral capillary tube;

measuring the length of one of the particles in the tube;

adaptively controlling on the basis of the length measurement at least one measurement point along the length of the one of the particles for a transverse measurement of the one of the particles; and forming an image at least at an imaging point;

measuring a transverse measure of the one of the particles at the imaging point from the image.

57. A measuring instrument for measuring particles in suspension the measuring instrument comprising:

a substantially equilateral capillary tube in which suspended particles are flowing one by one;

a first camera being arranged to form a real image of a particle in the tube;

a computer for measuring the length of the particle based on the real image taken by the first camera, and for determining on the basis of the length measurement of the particle at least at one measurement point along the particle for a transverse measure;

a second camera being controlled by the computer to form a real image of the particle at an imaging point in the tube for measuring the transverse measure of the particle; and a measuring instrument adaptively controlled to measure the transverse measure of the particle at the determined measurement and imaging points using the image of the second camera.

* * * * *